United States Patent
Kumar et al.

(10) Patent No.: US 7,078,430 B2
(45) Date of Patent: Jul. 18, 2006

(54) HMG COA-REDUCTASE INHIBITORS

(75) Inventors: Yatendra Kumar, Gurgaon (IN); Ram Chander Aryan, New Delhi (IN); Jitendra Sattigeri, Gurgaon (IN); Mohammad Salman, Gurgaon (IN); Gowri Shankar, New Delhi (IN); Kumar Hari Bhushan, Bihar (IN); Bhargav R. Panyda, Gujarat (IN); Ramnik Sharma, Ambala (IN)

(73) Assignee: Ranbaxy Laboratories Limited, Haryana (IN)

( * ) Notice: Subject to any disclaimer, the term of this patent is extended or adjusted under 35 U.S.C. 154(b) by 42 days.

(21) Appl. No.: 10/429,609

(22) Filed: May 5, 2003

(65) Prior Publication Data
US 2004/0019100 A1    Jan. 29, 2004

(30) Foreign Application Priority Data
Jul. 8, 2002    (IN) ................................ 724/Del/02

(51) Int. Cl.
*A61K 31/40* (2006.01)
*C07D 405/00* (2006.01)

(52) U.S. Cl. ...................................... 514/422; 548/517
(58) Field of Classification Search ................ 514/422; 548/517
See application file for complete search history.

(56) References Cited

U.S. PATENT DOCUMENTS

| | | | | |
|---|---|---|---|---|
| 4,681,893 A | * | 7/1987 | Roth | 514/422 |
| 5,273,995 A | | 12/1993 | Roth | 514/422 |
| 5,298,627 A | | 3/1994 | Butler et al. | 548/517 |
| 5,385,929 A | | 1/1995 | Bjorge et al. | 514/422 |

OTHER PUBLICATIONS

Lea and McTavish, "Atorvastatin. A Review of its Pharmacology and Theraputic Potential in the Management of Hyperlipidaemias", *Drugs*, 53(5):828-847 (1997).

Kubo and Strott, "Differential Activity of 3-Hydroxy-3-Methylglutaryl Coenzyme A Reductase in Zones of the Adrenal Cortex", *Endocrinology*; 120(1):214-221 (1987).

Heller and Gould, "Solubilization and Partial Purification of Hepatic 3-Hydroxy-3-Methylglutaryl Coenzyme A Reductase", *Biochemical and Biophysical Research Communications*, 50(3):859-865 (1973).

C.B. Reese, "Chapter 3—Protection of Alcoholic Hydroxyl Groups and Glycol Systems" *Protective Groups in Organic Chemistry*, Edited by J.F.W. McOmie, Plenum Press, New York, NY (1973).

* cited by examiner

*Primary Examiner*—Kamal A. Saeed
(74) *Attorney, Agent, or Firm*—Jayadeep R. Deshmukh, Esq.; George E. Heibel, Esq.

(57) ABSTRACT

The invention relates to particular hydroxyl and protected hydroxyl derivatives of compounds known to be useful as HMG CoA-reductase inhibitors. In particular, herein are provided hydroxyl and protected hydroxyl compounds of Formula I

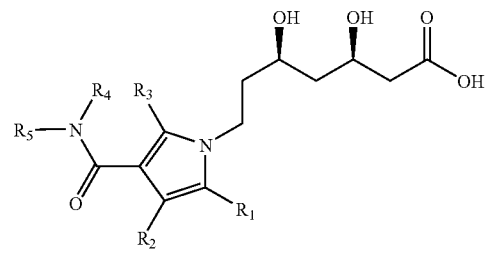

Formula I and their corresponding lactones.

66 Claims, No Drawings

HMG COA-REDUCTASE INHIBITORS

FIELD OF THE INVENTION

The invention relates to particular hydroxyl and protected hydroxyl derivatives of compounds known to be useful as HMG CoA-reductase inhibitors.

BACKGROUND OF THE INVENTION

U.S. Pat. No. 4,681,893 discloses compounds including trans (±)-5-(4-fluorophenyl)-2-(1-methylethyl)-N, 4-diphenyl-1-[2-(tetrahydro-4-hydroxy-6-oxo-2H-pyran-2-yl) ethyl]-1H-pyrrol e-3-carboxamides, and the corresponding ring-opened acids derived therefrom, and pharmaceutically acceptable salts thereof. U.S. Pat. No. 5,273,995 describes the optically pure compound, [R-(R*,R*)]-2-(4-fluorophenyl)-β,δ-dihydroxy-5-(1-methylethyl)-3-phenyl-4-(phenylamino)carbonyl]-1H-pyrrole-1-heptanoic acid, pharmaceutically acceptable salts thereof, and the corresponding cyclized lactone forms. U.S. Pat. No. 5,385,929 discloses certain phenyl hydroxy derivatives of the compounds disclosed in U.S. Pat. No. 5,273,995, and that such phenyl hydroxy derivatives are also active as inhibitors of the biosynthesis of cholesterol.

SUMMARY OF THE INVENTION

Herein are provided new hydroxylated and protected hydroxylated compounds which act as inhibitors of the activity of HMG CoA-reductase, formulations containing the same, and methods for treating subjects suffering from hypercholesterolemia by administering directly such hydroxylated or protected hydroxylated compounds. In particular, herein are provided hydroxyl and protected hydroxyl compounds of Formula I Formula I

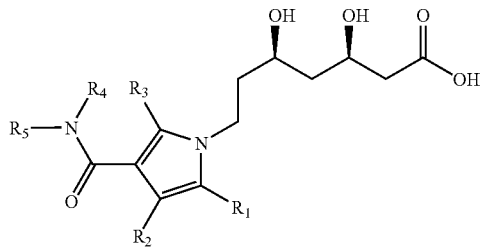

and the corresponding lactones of Formula II

Formula II

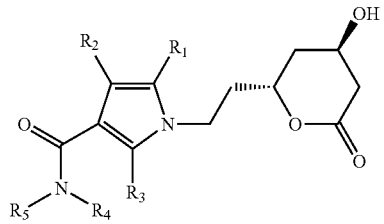

where $R_1$ is $C_1$–$C_6$ alkyl; $C_3$–$C_7$ cycloalkyl; or unsubstituted or optionally substituted phenyl having the phenyl substituents halogen, $C_1$–$C_6$ alkyl, cyano or $C_1$–$C_3$ perfluoroalkyl;

$R_2$ is unsubstituted or optionally substituted phenyl having the phenyl substituents cyano; acetyl; or unsubstituted or optionally substituted amino having the amino substituents $C_1$–$C_6$ alkyl, $C_3$–$C_7$ cycloalkyl, or acetyl;

$R_3$ is unsubstituted or optionally substituted $C_1$–$C_6$ alkyl or $C_3$–$C_7$ cycloalkyl having the alkyl or cycloalkyl substituents halogen; perfluoroalkyl; unsubstituted or optionally substituted amino having the amino substituents $C_1$–$C_6$ alkyl, $C_3$–$C_7$ cycloalkyl, or acetyl; hydroxyl; $C_1$–$C_3$ alkoxy; protected hydroxyl; carboxyl; or $C_1$–$C_3$ alkoxycarbonyl;

$R_4$ and $R_5$ are independently hydrogen; $C_1$–$C_6$ alkyl; $C_1$–$C_3$ cycloalkyl; or

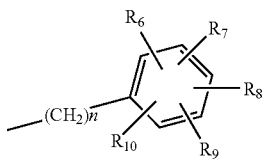

wherein n=0 or 1 and $R_6$, $R_7$, $R_8$, $R_9$ & $R_{10}$ are independently selected from hydrogen; halogen; hydroxyl; protected hydroxyl; $C_1$–$C_6$ alkoxy; unsubstituted or optionally substituted $C_1$–$C_6$ alkyl having the alkyl substituents hydroxyl or protected hydroxyl; unsubstituted or optionally substituted amino having the amino substituents $SO_2$ $R_{11}$, $CO$ $R_{11}$, $CONH$ $R_{11}$, wherein $R_{11}$ is $C_1$–$C_6$ alkyl, or aryl; cyano; acetyl; trifluoromethyl; $C_1$–$C_6$ alkoxycarbonyl; or two successive positions of the phenyl ring substituted by an unsubstituted or optionally substituted methylene dioxy group having the structure

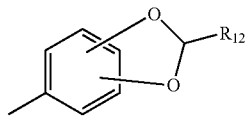

wherein $R_{12}$ is $C_1$–$C_3$ alkyl;

and the pharmaceutically acceptable salts, tautomers, racemates, pure enantiomers or diastereoisomers, and solvates thereof. In particular embodiments, when n=0 at least one of $R_6$, $R_7$, $R_8$, $R_9$ & $R_{10}$ is hydroxyl or protected hydroxyl, and in other particular embodiments, if only one of $R_6$, $R_7$, $R_8$, $R_9$ & $R_{10}$ is hydroxyl or protected hydroxyl, then at least one of the other substituents is not hydrogen.

These compounda are believed to be potent inhibitors of cholesterol biosynthesis by virtue of their ability to inhibit the enzyme 3-hydroxy-3-methylglutaryl coenzyme A reductase (HMG-CoA reductase). Pharmaceutical formulations comprising heptanoic acids of Formula I, or lactones of Formula II, and their pharmaceutically acceptable salts tautomers, racemates, pure enantiomers or diastereoisomers, and solvates thereofe, together with a pharmaceutically acceptable carrier are provided herein. Further, methods of treating mammals suffering from conditions of hypercholesterolemia by administering pharmaceutical formulations described herein are provided.

DETAILED DESCRIPTION OF THE INVENTION

Atorvastatin, a HMG CoA reductase inhibitor, has been reported to be metabolize, by the action of cytochrome P450 3A4, to ortho- and parahydroxylated derivatives and various beta-oxidation products. In vitro inhibition of HMG-CoA reductase by ortho- and parahydroxylated metabolites can occur. These compounds are metabolized in vivo to particular phenyl hydroxy derivatives, which are active. It is reported that almost 70% of the HMG Co-A reductase inhibition associated with atorvastatin is attributable to the action of active metabolites (*Drug*, (1991), 53(5), 828–847).

The compounds described herein can be in their ring-opened hydroxy-acid forms, or in the form of their pharmaceutically acceptable salts, solvates, tautomers and N-oxides. The chiral centers can be either racemic or stereo-pure states. Pharmaceutically acceptable salts include sodium, potassium, magnesium, zinc, calcium, zinc, iron, aluminium, ammonium, quaternary ammonium, etc. Salts with organic bases, such as N-methylglucamine, etc. can also be used.

In one embodiment, there are provided compounds of Formula I

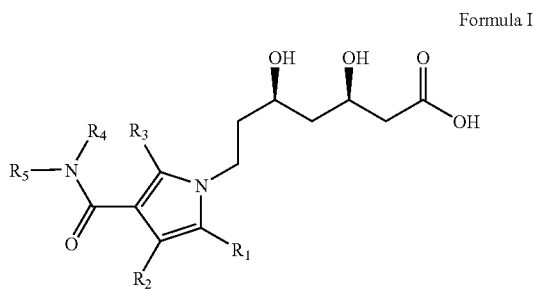

Formula I wherein $R_1$, $R_2$, $R_3$, $R_4$ and $R_5$ are as defined above, and the pharmaceutically acceptable salts, tautomers, racemates, pure enantiomers or diastereoisomers, and solvates of the compounds of Formula I.

In a further embodiment, provided herein are compounds of Formula II

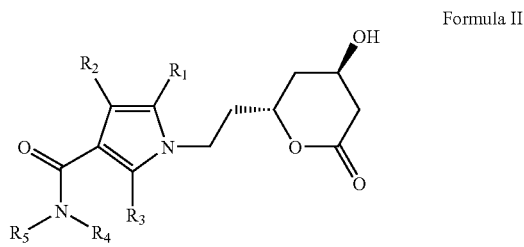

Formula II wherein $R_1$, $R_2$, $R_3$, $R_4$ and $R_5$ are as defined above, and the tautomers, racemates, pure enantiomers or diastereoisomers, and solvates of the compounds of Formula II.

In a further embodiment, pharmaceutical preparations of the disclosed compounds are provided. In yet a further embodiment, methods of inhibiting cholesterol synthesis in an animal comprising administering the disclosed compounds or pharmaceutical compositions are provided. In still a further embodiment, methods of treating a mammal suffering from conditions of hypercholesterolemia by administering the disclosed compounds or pharmaceutical compositions are provided.

The following compounds are illustrative of particular embodiments:

7-[3-(2,4-dimethoxyphenylcarbamoyl)-5-(4-fluorophenyl)-2-(1-methylethyl)-4-phenyl-pyrrol-1-yl]-3R,5R-dihydroxy-heptanoic acid calcium salt 7-[3-(2-methoxy-4-hydroxyphenylcarbamoyl)-5-(4-fluorophenyl)-2-(1-methylethyl)-4-phenyl-pyrrol-1-yl]-3R,5R-dihydroxy-heptanoic acid calcium salt 7-[3-(2,4-dihydroxyphenylcarbamoyl)-5-(4-fluorophenyl)-2-(1-methylethyl)-4-phenyl-pyrrol-1-yl]-3R,5R-dihydroxy-heptanoic acid calcium salt 7-[2-cyclopropyl-3-(2,4-dimethoxyphenylcarbamoyl)-5-(4-fluorophenyl)-4-phenyl-pyrrol-1-yl]-3R,5R-dihydroxy-heptanoic acid calcium salt 7-[3-(2,4-dimethoxyphenylcarbamoyl)-4,5-diphenyl5-(4-fluorophenyl)-2-(1-methylethyl)-pyrrol-1-yl]-3R,5R-dihydroxy-heptanoic acid calcium salt 7-[4,5-bis(4-fluorophenyl)-3-(2,4-dimethoxyphenylcarbamoyl)-2-(1-methylethyl)-pyrrol-1-yl]-3R,5R-dihydroxy-heptanoic acid calcium salt 7-[3-(3,5-dimethoxyphenylcarbamoyl)-5-(4-fluorophenyl)-2-(1-methylethyl)-4-phenyl-pyrrol-1-yl]-3R,5R-dihydroxy-heptanoic acid calcium salt 7-[3-(3,4-dimethoxyphenylcarbamoyl)-5-(4-fluorophenyl)-2-(1-methylethyl)-4-phenyl-pyrrol-1-yl]-3R,5R-dihydroxy-heptanoic acid calcium salt 7-[4,5-bis(4-fluorophenyl)-2-cyclopropyl-3-(2,4-dimethoxyphenylcarbamoyl)-pyrrol-1-yl]-3R,5R-dihydroxy-heptanoic acid calcium salt 7-[5-(3,4-difluorophenyl)-3-(2,4-dihydroxyphenylcarbamoyl)-2-(1-methylethyl)-4-(4-fluorophenyl)-pyrrol-1-yl]-3R,5R-dihydroxy-heptanoic acid calcium salt 7-[2-cyclopropyl-5-(3,4-difluorophenyl)-3-(2,4-dihydroxyphenylcarbamoyl)-4-(4-fluorophenyl)-pyrrol-1-yl]-3R,5R-dihydroxy-heptanoic acid calcium salt 7-[5-(3,4-difluorophenyl)-3-(2,4-dihydroxyphenylcarbamoyl)-2-(1-methylethyl)-4-phenyl-pyrrol-1-yl]-3R,5R-dihydroxy-heptanoic acid calcium salt 7-[5-(3,4-difluorophenyl)-3-(2,4-dimethoxycarbamoyl)-4-(4-fluorophenyl)-2-(1-methylethyl)-pyrrol-1-yl]-3R,5R-dihydroxy-heptanoic acid calcium salt 7-[2-cyclopropyl-5-(3,4-difluorophenyl)-3-(2,4-dimethoxycarbamoyl)-4-(4-fluorophenyl)-pyrrol-1-yl]-3R,5R-dihydroxy-heptanoic acid calcium salt 7-[5-(3,4-difluorophenyl)-3-(2,4-dimethoxycarbamoyl)-2-(1-methylethyl)-4-phenyl-pyrrol-1-yl]-3R,5R-dihydroxy-heptanoic acid calcium salt The compounds of this invention can be used as hypocholesterolemic or hypolipidemic agents by virtue of their ability to inhibit the biosynthesis of cholesterol through inhibition of the enzyme 3-hydroxy-3-methylglutaryl-coenzyme A reductase (HMG-CoA reductase).

The compounds described herein have been screened in an in-vitro HMG-CoA reductase enzyme assay as described by Kubo et al., *Endocrinology*, 120, 214 (1987); and Hellar et al., *Biochem. Biophys. Res. Comm.*, 50, 859 (1973).

HMG-CoA reductase is regarded as a rate-limiting enzyme in cholesterol biosynthesis, catalyzing the following reaction:

[$^{14}$C]HMG-CoA+2NADPH+2H+[$^{14}$C]mevanolate+ CoA+2NADP+microsomes, utilizing 2.5 mM [$^{14}$C]HMG-CoA as a substrate.

The reaction was carried out in presence of 100 mM $KH_2PO_4$, 20 mM G-6-P, 2.5 mM NADPH, 10 mM EDTA, 5 mM DTT and 1.4 G-6-P dehydrogenase, at 37° C. for 15 minutes and quantitating [$^{14}$C] mevalonate as an end product. For IC$_{50}$ determinations, the compounds were dissolved in 1% dimethylsulfoxide, and were preincubated with liver microsomes at 37° C. for 30 minutes. The activity of several representative examples of particular compounds appears in Table 1, and is compared with that of atorvastatin.

TABLE 1

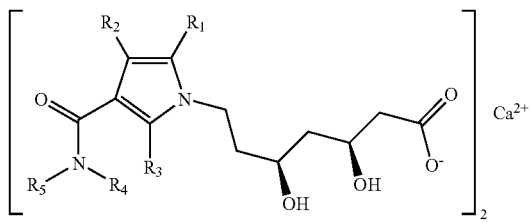

| S.No. | R$_1$ | R$_2$ | R$_3$ | R$_4$ | R$_5$ | IC$_{50}$(pM) |
|---|---|---|---|---|---|---|
| 1 | 4-Fluorophenyl | Phenyl | Isopropyl | Hydrogen | 2-Methoxy-4-hydroxyphenyl | 22 |
| 2 | 4-Fluorophenyl | Phenyl | Isopropyl | Hydrogen | 2,4-Dihydroxyphenyl | 7.93 |
| 3 | 4-Fluorophenyl | Phenyl | Cyclopropyl | Hydrogen | 2,4-Dimethoxyphenyl | 9.48 |
| 4 | 4-Fluorophenyl | Phenyl | Isopropyl | Hydrogen | 2,4-Dimethoxyphenyl | 49 (mM) |
| 5 | Phenyl | Phenyl | Isopropyl | Hydrogen | 2,4-Dimethoxyphenyl | 56.3 |
| 6 | 4-Fluorophenyl | 4-Fluorophenyl | Isopropyl | Hydrogen | 2,4-Dimethoxyphenyl | 17.2 |
| Atorvastatin | 4-Fluorophenyl | Phenyl | Isopropyl | Hydrogen | Phenyl | 64.6 |

The compounds disclosed herein can be formulated with conventional carriers and excipients, and administered to animals for inhibiting the biosynthesis of cholesterol. For preparing pharmaceutical compositions from the disclosed compounds, inert, pharmaceutically acceptable carriers can be either solid or liquid. Solid form preparations include powders, tablets, dispersible granules, capsules, cachets, and suppositories. A solid carrier can be one or more substances which may also act as diluents, flavoring agents, solubilizers, lubricants, suspending agents, binders, or tablet disintegrating agents; it can also be an encapsulating material. In powders, the carrier is a finely divided solid which is in a mixture with the finely divided active component. In tablets, the active compound is mixed with the carrier having the necessary binding properties in suitable proportions and compacted in the shape and size desired. For preparing suppositories, a low-melting wax such as a mixture of fatty acid glycerides and cocoa butter is first melted, and the active ingredient is dispersed therein by, for example, stirring. The molten homogeneous mixture is then poured into convenient sized molds and allowed to cool and solidify.

Powders and tablets can contain between about 5 and about 70% by weight of the active ingredient. Suitable carriers are magnesium carbonate, magnesium stearate, talc, lactose, sugar, pectin, dextrin, starch, tragacanth, methyl cellulose, sodium carboxymethyl cellulose, a low-melting wax, cocoa butter, and the like.

The term "preparation" is intended to include the formulation of the active compound with encapsulating material as a carrier providing a capsule in which the active component (with or without other carriers) is surrounded by a carrier, which is thus in association with it. In a similar manner, cachets are also included. Tablets, powders, cachets, and capsules can be used as solid dosage forms suitable for oral administration.

Liquid form preparations include solutions suitable for oral or parenteral administration, or suspensions and emulsions suitable for oral administration. Sterile water solutions of the active component or sterile solutions of the active component in solvents comprising water, ethanol, or propylene glycol may be mentioned as examples of liquid preparations suitable for parenteral administration. Sterile solutions may be prepared by dissolving the active component in the desired solvent system, and then passing the resulting solution through a membrane filter to sterilize it or, alternatively, by dissolving the sterile compound in a previously sterilized solvent under sterile conditions. Aqueous solutions for oral administration can be prepared by dissolving the active compound in water and adding suitable flavorants, coloring agents, stabilizers, and thickening agents as desired. Aqueous suspensions for oral use can be made by dispersing the finely divided active component in water together with a viscous material such as natural or synthetic gums, resins, methyl cellulose, sodium carboxymethyl cellulose, and other suspending agents known to the pharmaceutical formulation art.

In particular embodiments, the pharmaceutical preparation is in unit dosage form. In such forms, the preparation can be divided into unit doses containing appropriate quantities of the active component. The unit dosage form can be a packaged preparation, the package containing discrete quantities of the preparation, for example, packeted tablets, capsules, and powders in vials or ampoules. The unit dosage form can also be a capsule, cachet, or tablet itself, or it can be the appropriate number of any of these packaged forms.

As used herein, the term "protected hydroxyl" refers to an oxygen atom attached to an organic radical that can be bonded to oxygen to prevent unwanted reactions at that site, yet can be removed when desired to generate a hydroxyl group. Typical examples of hydroxyl protecting groups include acyl moieties such as acetyl, chloroacetyl, and dichloroacetyl; as well as ether-forming groups such as benzyl, trimethylsilyl, and the like. Such readily removable hydroxy protecting groups are more fully described by H. Haslam in "Protective Groups in Organic Chemistry," McOmie, J. F. W., Ed., Plenum Press, New York, N.Y., 1973, Chapter 3.

The following examples illustrate particular methods for preparing the compounds disclosed herein. These examples are illustrative and do not limit the scope of the invention. The protected derivatives of Formula I can be deprotected by conventional methods known in the literature.

EXAMPLE 1

Preparation of 7[3-(3,5-dimethoxy-phenylcarbamoyl)-5-(4-fluorophenyl)-2-(1-methylethyl)-4-phenyl-pyrrol-1-yl]-3R,5R-dihydroxy-heptanoic acid sodium salt Step A: Preparation of 4-methyl-3-oxo-N-(3,5-dimethoxyphenyl)-2-(phenylmethylene)pentamide (V)

3,5-dimethoxyaniline (10 g, 65 mmol), methyl isobutyryl acetate (9.11 g, 63 mmoles) and 1,2-ethylenediamine (~0.05 ml) were refluxed together in toluene (50 ml) in a flask equipped with a Dean-Stark apparatus. Water was removed azeotropically by refluxing for about 18 hours until reaction completion. The reaction mass was cooled to about 40° C. Toluene was recovered under reduced pressure to obtain a residue which was then dissolved in ethyl acetate (200 ml). The ethyl acetate layer was washed with diluted HCl (10%, 35 ml×2) and finally with saturated brine (35 ml). The organic layer was concentrated under reduced pressure. The oily mass obtained was triturated to obtain white solid (12.8 g) which was taken up in hexane (65 ml) and to it β-alanine, glacial acetic acid (1.4 ml), and benzaldehyde (5.2 g, 49 mmol) were added. The mixture was refluxed in a flask equipped with a Dean-Stark apparatus to remove water azeotropically. After the completion of reaction, solid separated out. The reaction mass was cooled, filtered and the product was recrystallized from isopropyl alcohol/hexane to yield the title product (11.62 g)

Step B: Preparation of 4-methyl-3-oxo-N-(3,5-dimethoxyphenyl)-2-[1-phenyl-2-(4-fluorophenyl)-2-oxo-ethyl]pentamide (VI)

The product from Step A (10 g) was taken up in isopropyl alcohol (40 ml) and to it 4-fluorobenzaldehyde (3.51 g, 28 mmol) and triethyl amine (1.67 g, 28 mmol) were added, followed by 3-ethyl-5-[2-hydroxylethyl)-4-ethylthiazolium bromide (7.14 g, 28 mmol). The reaction mixture was refluxed for about 30 hour at 80–81° until reaction completion. The reaction mixture was cooled to about 40–45° C. Isopropyl alcohol was recovered under reduced pressure. The oily product was dissolved in ethyl acetate and washed with water, dilute hydrochloric acid, followed with washing with brine. The organic layer was concentrated under reduced pressure to obtain an oily product (12.5 g)

Step C: Preparation of (2R-trans)-5-(4-fluorophenyl)-2-[1-methylethyl)-N-(3,5-dimethoxyphenyl)-4-phenyl-1-[2-(tetrahydro-4-hydroxy-6-oxo-2H-pyran-2-yl)ethyl]-1H pyrrole-3-carboxamide (VII) (Isolated as the Open Chain Hydroxyl Acid)

The oily product from Step B (12.5 g, 26.2 mmol) was taken up in a solvent mixture (128 ml) of heptane, toluene and tetrahydrofuran in ratio of 7:1:1 respectively. To this, a side chain amine derivative, i.e., (4R,cis)-1,1-dimethylethyl-6-(2-aminoethyl)-2,2-dimethyl-1,3-dioxane-4-acetate (prepared as mentioned in lit.) 8.3 g, 30 mmol was added, followed by addition of pivalic acid (3.17 g, 31 mmol). The reaction mixture was refluxed at 85–90° C. for about 15 hours. After the completion of the reaction, it was cooled to room temperature. Dichloromethane (100 ml) was added to the reaction mass, which was then washed with HCl (10%), followed by saturated sodium bicarbonate solution and brine washings. The organic layer was concentrated under reduced pressure and the residue dissolved in methanol (300 ml). Water (30 ml) and concentrated hydrochloric acid (30 ml) were added to the above methanolic solution. The mixture was stirred at 40° C. for about 2 hours. Methanol was removed under reduced pressure. The oily product was extracted into ethyl acetate, and was washed with water and brine. The ethyl acetate layer was concentrated under reduced pressure to obtain an oily mass (14.5 gm), which was dissolved in methanol (200 ml) and to this a sodium hydroxide solution (4.5 g in 45 ml water) was added. The reaction mixture was stirred at room temperature for 1.5 hours. Methanol was recovered under reduced pressure. Water was added and the aqueous layer was washed with ethyl acetate. The aqueous layer was acidified to pH 2–3 with dilute HCl. The product was extracted with ethyl acetate. Ethyl acetate layer was concentrated under reduced pressure to obtain an oily product (7.3 g).

Step D: Preparation of 7-[3-(3,5-dimethoxy-phenylcarbamoyl)-5-(4-fluorophenyl)-2-(1-methylethyl)-4-phenyl-pyrrol-1-yl]-3R,5R-dihydroxy-heptanoic Acid Sodium Salt The product from Step C was dissolved in tetrahydrofuran (73 ml) and was cooled to about 0 to 5° C. Water (14.6 g) was added followed by addition of sodium hydroxide solution (0.47 g in 45 ml water) at 0 to 5° C., and the mixture was stirred at 0 to 5° C. for about 2 hours while maintaining pH ~11–12. The pH was then adjusted to ~8.5 to 9.0 and tetrahydrofuran was removed under reduced pressure. The aqueous layer was washed with methyl t-butyl ether (30 ml×4). The aqueous layer containing the sodium salt of the product was taken further for the formation of calcium salt.

Step E: Preparation of 7-[3-(3,5-dimethoxyphenyl carbamoyl)-5-(4-fluorophenyl)-2-(1-methylethyl)-4-phenyl-pyrrol-1-yl]-3R,5R-dihydroxy-heptanoic Acid Calcium Salt An aqueous solution of the sodium salt from Step D was heated to 50° C. To this solution, calcium acetate solution (0.94 g in 35 ml of water) was added and the mixture was stirred for about 30 minutes and then cooled to room temperature. The reaction mixture was stirred for 1 hour, and then was filtered and washed with water (30 ml×3). The solid product was dried under reduced pressure of <10 mm/Hg at 45° C. to obtain the calcium salt of the product (4.6 g).

The mass spectrum of the product showed a mass peak (M$^+$+1): 619. The 'HNMR spectrum, DMSO-d$_6$ (δ, ppm), showed the following peaks: 1.18–1.30 (m, 2H), 1.38 (d, 6H), 1.45–1.70 (m, 2H), 1.93 (dd, 1H), 2.10 (dd, 1H), 3.2–3.3 (m, 1H), 3.50–3.60 (m, 1H), 3.7 (s, 6H), 3.72–3.80 (m, 2H), 3.82–4.0 (m, 1H), 6.18 (s, 1H), 6.8 (s, 2H), 7.0–7.4 (m, 9H), 9.75 (s, 1H). The infrared spectrum showed peaks at (K Br) cm$^{-1}$: 3407, 2960, 1664, 1602, 1560, 1508, 1450.

EXAMPLE 2

Preparation of 7-[3-(2,4-dimethoxyphenyl carbamoyl)-5-(4-fluorophenyl)-2-(cyclopropyl)-4-(4-fluorophenyl)-pyrrol-1-yl]-3R,5R-dihydroxy-heptanoic Acid Calcium salt The title compound was prepared by following a process analogous to the one described in Example 1. Equimolar amounts of 2,4-Dimethoxyaniline, methyl 3-cyclopropyl-3-oxo propionate, and 4-fluorobenzaldehyde were used in place of 3,5-dimethoxyaniline and methyl isobutyryl acetate, and benzaldehyde respectively.

The mass spectrum of the product showed a mass peak (M$^+$+1): 635. The 'HNMR spectrum, DMSO-d$_6$ (δ, ppm) showed the following peaks: 0.70 (d, 2H), 0.95 (d, 2H), 1.10–1.25 (m, 1H), 1.35–1.42 (m, 1H), 1.45–1.60 (m, 2H), 1.85–1.97 (m, 2H), 2.07 (dd, 1H), 3.45–3.54 (m, 1H), 3.6–3.8 (m, 1H), 3.67 (s, 3H), 3.73 (s, 3H), 3.90–4.12 (m, 2H), 6.46 (dd, 1H), 6.55 (bs, 1H), 6.90–7.30 (m, 8H), 7.77 (d, 1H), 8.32 (s, 1H). The infrared spectrum showed peaks at (KBr) cm-¹: 3407, 2939, 1655, 1601, 1562, 1517.

EXAMPLE 3

Preparation of 7-[3-(2,4-dimethoxyphenyl carbamoyl)-5-(4-fluorophenyl)-2-(cyclopropyl)-4-phenyl-pyrrol-1-yl]-3R,5R-dihydroxy-heptanoic acid calcium salt The title compound was prepared by following a process analogous to the one described in Example 1, replacing methyl 3-cyclopropyl-3-oxo propionate with an equimolar amount of methyl isobutyryl acetate.

The mass spectrum of the product showed a mass peak (M⁺+1): 617.6. The 'HNMR spectrum, DMSO-$d_6$ (δ, ppm) showed the following peaks: 0.70 (d, 2H), 0.94 (d, 2H), 1.15–1.28 (m, 1H), 1.30–1.42 (m, 1H), 1.42–1.70 (m, 2H), 1.85–1.98 (m, 2H), 2.0–2.12 (dd, 1H), 3.45–3.58 (m, 1H), 3.65 (s, 3H), 3.73 (s, 3H), 3.66–3.80 (m, 1H), 3.9–4.2 (m, 2H), 6.46 (d, 1H), 6.53 (s, 1H), 7.0–7.3 (m, 9H), 7.79 (d, 1H), 8.28 (s, 1H). The infrared spectrum showed peaks at (KBr) cm-¹: 3397, 2937, 1649, 1599, 1520, 1412.

EXAMPLE 4

Preparation of 7-[4,5-bis(4-fluorophenyl)-3-(2,4-dimethoxyphenylcarbamoyl)-2-(1-methylethyl)-pyrrol-1-yl]-3R,5R-dihydroxy-heptanoic acid, calcium salt The title compound was prepared by following a process analogous to the one described in Example 1, replacing the benzaldehyde in Step A with an equimolar amount of 4-flurobenzaldehyde.

The mass spectrum of the product showed a mass peak (M⁺+1): 637.5. The 'HNMR spectrum, DMSO-$d_6$ (δ, ppm) showed the following peaks: 1.10–1.28 (m, 1H), 1.30–1.40 (m, 1H), 1.41 (d, 6H), 1.38–1.65 (m, 2H), 1.90–1.98 (m, 1H), 2.00–2.10 (dd, 1H), 3.25–3.43 (m, 1H), 3.45–3.60 (m, 1H), 3.54 (s, 3H), 3.60–3.80 (m, 2H), 3.71 (s, 3H), 3.80–4.00 (m, 1H), 6.40–6.52 (m, 2H), 6.90–7.35 (m, 8H), 7.82 (d, 1H), 7.94 (s, 1H). The infrared spectrum showed peaks at (KBr) cm-¹: 3408, 2929, 1653, 1518, 1281.

EXAMPLE 5

Preparation of 7-[3-(2,4-dimethoxyphenylcarbamoyl)-4,5-diphenyl-2-(1-methylethyl)-pyrrol-1-yl]-3R,5R-dihydroxy-heptanoic acid calcium salt The title compound was prepared by following a process analogous to the one described in Example 1, replacing the 4-flurobenzaldehye in Step B with an equimolar amount of benzaldehyde.

The mass spectrum of the product showed a mass peak (M⁺+1): 601.5. The 'HNMR spectrum, DMSO-$d_6$ (δ, ppm) showed the following peaks: 1.10–1.25 (m, 1H), 1.30–1.40 (m, 1H), 1.41 (d, 6H), 1.48–1.68 (m, 2H), 1.90–2.00 (m, 1H), 2.02–2.12 (dd, 1H), 3.25–3.43 (m, 1H), 3.45–3.52 (m, 1H), 3.51 (s, 3H), 3.60–3.85 (m, 2H), 3.70 (s, 3H), 3.80–4.05 (m, 1H), 6.40–6.50 (m, 2H), 6.90–7.40 (m, 10H), 7.80–7.90 (m, 2H). The infrared spectrum showed peaks at (KBr) cm-¹: 3405, 2958, 1654, 1601, 1559, 1522, 1458, 1412.

We claim:
1. A compound of formula 1

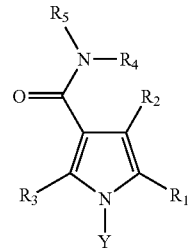

Formula I wherein
$R_1$ is $C_1$–$C_6$ alkyl; $C_3$–$C_7$ cycloalkyl; or unsubstituted or optionally substituted phenyl having the phenyl substituents halogen, $C_1$–$C_6$ alkyl, cyano or $C_1$–$C_3$ perfluoroalkyl;
$R_2$ is unsubstituted or optionally substituted phenyl having the phenyl substituents cyano; acetyl; or unsubstituted or optionally substituted amino having the amino substituents $C_1$–$C_6$ alkyl, $C_3$–$C_7$ cycloalkyl, or acetyl;
$R_3$ is unsubstituted or optionally substituted $C_1$–$C_6$ alkyl or $C_3$–$C_7$ cycloalkyl having the alkyl or cycloalkyl substituents halogen; perfluoroalkyl; unsubstituted or optionally substituted amino having the amino substituents $C_1$–$C_6$ alkyl, $C_3$–$C_7$ cycloalkyl, or acetyl; hydroxyl; $C_1$–$C_3$ alkoxy; protected hydroxyl; carboxyl; or $C_1$–$C_3$ alkoxycarbonyl;
$R_4$ and $R_5$ are independently hydrogen; $C_1$–$C_6$ alkyl; $C_1$–$C_3$ cycloalkyl; or

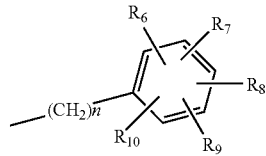

wherein n=0 or 1 and $R_6$, $R_7$, $R_8$, $R_9$ & $R_{10}$ are independently selected from hydrogen; halogen; hydroxyl; protected hydroxyl; $C_1$–$C_6$ alkoxy; unsubstituted or optionally substituted $C_1$–$C_6$ alkyl having the alkyl substituents hydroxyl or protected hydroxyl; unsubstituted or optionally substituted amino having the amino substituents $SO_2 R_{11}$, $COR_{11}$, $CONH R_{11}$, wherein $R_{11}$ is $C_1$–$C_6$ alkyl, or aryl; cyano; acetyl; trifluoromethyl; $C_1$–$C_6$ alkoxycarbonyl; or two successive positions of the phenyl ring substituted by an unsubstituted or optionally substituted methylene dioxy group having the structure

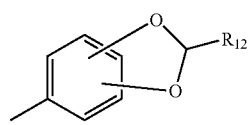

wherein $R_{12}$ is $C_1$–$C_3$ alkyl; with the provisio that when n=0 at least one of $R_6$, $R_7$, $R_8$, $R_9$ & $R_{10}$ is hydroxyl or protected hydroxyl, with the further provisio that if only one of $R_6$, $R_7$, $R_8$, $R_9$ & $R_{10}$ is hydroxyl or protected hydroxyl, then at least one of the other substituents is not hydrogen;
wherein Y is

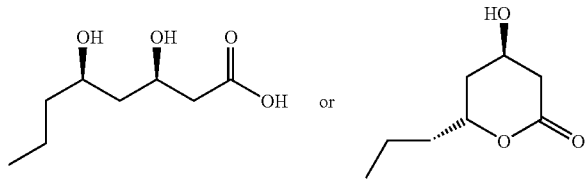

including the tautomers, racemates, pure enantiomers and diastereoisomers, N-oxides, or solvates of the compound of formula I.

2. A compound of claim 1 wherein $R_1$ is phenyl.

3. A compound of claim 1 wherein $R_1$ is phenyl substituted with one or more halogens or cyano groups.

4. A compound of claim 1 wherein $R_1$ is phenyl substituted with one or more halogens.

5. A compound of claim 1 wherein $R_1$ is phenyl substituted with one or more fluorine atoms.

6. A compound of claim 1 wherein $R_1$ is 4-fluorophenyl.

7. A compound of claim 1 wherein $R_2$ is phenyl.

8. A compound of claim 1 wherein $R_2$ is phenyl substituted with one or more halogens or cyano groups.

9. A compound of claim 1 wherein $R_2$ is phenyl substituted with one or more halogens.

10. A compound of claim 1 wherein $R_2$ is phenyl substituted with one or more fluorine atoms.

11. A compound of claim 1 wherein $R_2$ is 4-fluorophenyl.

12. A compound of claim 1 wherein $R_3$ is $C_1$–$C_6$ alkyl or $C_3$–$C_7$ cycloalkyl.

13. A compound of claim 1 wherein $R_3$ is 2-methylethyl.

14. A compound of claim 1 wherein $R_3$ is cyclopropyl.

15. A compound of claim 1 wherein $R_4$ and $R_5$ are independently hydrogen.

16. A compound of claim 1 wherein $R_4$ and $R_5$ are independently phenyl.

17. A compound of claim 1 wherein $R_4$ and $R_5$ are independently phenyl substituted with a hydroxyl group and at least one or more halogens or cyano groups.

18. A compound of claim 1 wherein $R_4$ and $R_5$ are independently phenyl substituted with a protected hydroxyl group and at least one or more halogens or cyano groups.

19. A compound of claim 1 wherein $R_4$ and $R_5$ are independently phenyl substituted with a methoxy group and at least one or more halogens or cyano groups.

20. A compound of claim 1 wherein $R_4$ and $R_5$ are independently phenyl substituted with two or more hydroxyl groups.

21. A compound of claim 1 wherein $R_4$ and $R_5$ are independently phenyl substituted with two or more methoxy groups.

22. A compound of claim 1 wherein $R_4$ is hydrogen and $R_5$ is phenyl substituted with a hydroxyl group and at least one or more halogens or cyano groups.

23. A compound of claim 1 wherein $R_4$ is hydrogen and $R_5$ is phenyl substituted with a methoxy group and at least one or more halogens or cyano groups.

24. A compound of claim 1 wherein $R_4$ is hydrogen and $R_5$ is phenyl substituted with two or more hydroxyl groups.

25. A compound of claim 1 wherein $R_4$ is hydrogen and $R_5$ is phenyl substituted with two or more methoxy groups.

26. A compound of claim 1 wherein $R_1$ and $R_2$ are independently phenyl or phenyl substituted with one or more fluorine atoms, $R_3$ is $C_1$–$C_6$ alkyl or $C_1$–$C_3$ cycloalkyl, $R_4$ and $R_5$ are independently phenyl substituted with a hydroxyl group and at least one or more halogens or cyano groups.

27. A compound of claim 1 wherein $R_1$ and $R_2$ are independently phenyl or phenyl substituted with one or more fluorine atoms, $R_3$ is $C_1$–$C_6$ alkyl or $C_1$–$C_3$ cycloalkyl, $R_4$ and $R_5$ are independently phenyl substituted with a protected hydroxyl group and at least one or more halogens or cyano groups.

28. A compound of claim 1 wherein $R_1$ and $R_2$ are independently phenyl or phenyl substituted with one or more fluorine atoms, $R_3$ is $C_1$–$C_6$ alkyl or $C_1$–$C_3$ cycloalkyl, $R_4$ and $R_5$ are independently phenyl substituted with two or more hydroxyl groups.

29. A compound of claim 1 wherein $R_1$ and $R_2$ are independently phenyl or phenyl substituted with one or more fluorine atoms, $R_3$ is $C_1$–$C_6$ alkyl or $C_1$–$C_3$ cycloalkyl, $R_4$ and $R_5$ are independently phenyl substituted with two or more protected hydroxyl groups.

30. A compound of claim 1 wherein $R_1$ and $R_2$ are independently phenyl or phenyl substituted with one or more fluorine atoms, $R_3$ is $C_1$–$C_6$ alkyl or $C_1$–$C_3$ cycloalkyl, $R_4$ and $R_5$ are independently phenyl substituted with two or more methoxy groups.

31. A compound of claim 1 wherein $R_1$ and $R_2$ are independently phenyl or phenyl substituted with one or more fluorine atoms, $R_3$ is $C_1$–$C_6$ alkyl or $C_1$–$C_3$ cycloalkyl, $R_4$ is hydrogen and $R_5$ is phenyl substituted with a hydroxyl group and at least one or more halogens or cyano groups.

32. A compound of claim 1 wherein $R_1$ and $R_2$ are independently phenyl or phenyl substituted with one or more fluorine atoms, $R_3$ is $C_1$–$C_6$ alkyl or $C_1$–$C_3$ cycloalkyl, $R_4$ is hydrogen and $R_5$ is phenyl substituted with a protected hydroxyl group and at least one or more halogens or cyano groups.

33. A compound of claim 1 wherein $R_1$ and $R_2$ are independently phenyl or phenyl substituted with one or more fluorine atoms, $R_3$ is $C_1$–$C_6$ alkyl or $C_1$–$C_3$ cycloalkyl, $R_4$ is hydrogen and $R_5$ is phenyl substituted with two or more hydroxyl groups.

34. A compound of claim 1 wherein $R_1$ and $R_2$ are independently phenyl or phenyl substituted with one or more fluorine atoms, $R_3$ is $C_1$–$C_6$ alkyl or $C_1$–$C_3$ cycloalkyl, $R_4$ is hydrogen and $R_5$ is phenyl substituted with two or more protected hydroxyl groups.

35. A compound of claim 1 wherein $R_1$ and $R_2$ are independently phenyl or phenyl substituted with one or more fluorine atoms, $R_3$ is $C_1$–$C_6$ alkyl or $C_1$–$C_3$ cycloalkyl, $R_4$ is hydrogen and $R_5$ is phenyl substituted with two or more methoxy groups.

36. A compound of claim 1 wherein $R_1$ and $R_2$ are independently selected from the group consisting of phenyl, monoflurophenyl and difluorophenyl, $R_3$ is $C_1$–$C_6$ alkyl or $C_1$–$C_3$ cycloalkyl, $R_4$ is hydrogen and $R_5$ is phenyl substituted with two or more hydroxyl groups.

37. A compound of claim 1 wherein $R_1$ and $R_2$ are independently selected from the group consisting of phenyl, monoflurophenyl and difluorophenyl, $R_3$ is $C_1$–$C_6$ alkyl or $C_1$–$C_3$ cycloalkyl, $R_4$ is hydrogen and $R_5$ is phenyl substituted with two or more protected hydroxyl groups.

38. A compound of claim 1 wherein $R_1$ and $R_2$ are independently selected from the group consisting of phenyl, monoflurophenyl and difluorophenyl, $R_3$ is $C_1$–$C_6$ alkyl, $R_4$ is hydrogen and $R_5$ is phenyl substituted with two or more methoxy groups.

39. A compound of claim 1 wherein $R_1$ and $R_2$ are independently selected from the group consisting of phenyl, monoflurophenyl and difluorophenyl, $R_3$ is $C_1$–$C_3$ cycloalkyl, $R_4$ is hydrogen and $R_5$ is phenyl substituted with two or more hydroxyl groups.

40. A compound of claim 1 wherein $R_1$ and $R_2$ are independently selected from the group consisting of phenyl, monoflurophenyl and difluorophenyl, $R_3$ is $C_1$–$C_3$ cycloalkyl, $R_4$ is hydrogen and $R_5$ is phenyl substituted with two or more protected hydroxyl groups.

41. A compound of claim 1 wherein $R_1$ and $R_2$ are independently selected from the group consisting of phenyl, monoflurophenyl and difluorophenyl, $R_3$ is $C_1$–$C_3$ cycloalkyl, $R_4$ is hydrogen and $R_5$ is phenyl substituted with two or more methoxy groups.

42. A compound of claim 1 wherein $R_1$ is 4-fluorophenyl or 3,4-difluorophenyl and $R_2$ is phenyl, $R_3$ is $C_1$–$C_6$ alkyl or $C_1$–$C_3$ cycloalkyl, $R_4$ is hydrogen and $R_5$ is phenyl substituted with two or more hydroxyl groups.

43. A compound of claim 1 wherein $R_1$ is 4-fluorophenyl or 3,4-difluorophenyl and $R_2$ is phenyl, $R_3$ is $C_1$–$C_6$ alkyl or $C_1$–$C_3$ cycloalkyl, $R_4$ is hydrogen and $R_5$ is phenyl substituted with two or more protected hydroxyl groups.

44. A compound of claim 1 wherein $R_1$ is 4-fluorophenyl or 3,4-difluorophenyl and $R_2$ is phenyl, $R_3$ is $C_1$–$C_6$ alkyl or $C_1$–$C_3$ cycloalkyl, $R_4$ is hydrogen and $R_5$ is phenyl substituted with two or more methoxy groups.

45. A compound of claim 1 wherein $R_1$ is phenyl and $R_2$ is 4-fluorophenyl, $R_3$ is $C_1$–$C_6$ alkyl or $C_1$–$C_3$ cycloalkyl, $R_4$ is hydrogen and $R_5$ is phenyl substituted with two or more hydroxyl groups.

46. A compound of claim 1 wherein $R_1$ is phenyl and $R_2$ is 4-fluorophenyl, $R_3$ is $C_1$–$C_6$ alkyl or $C_1$–$C_3$ cycloalkyl, $R_4$ is hydrogen and $R_5$ is phenyl substituted with two or more protected hydroxyl groups.

47. A compound of claim 1 wherein $R_1$ is phenyl and $R_2$ is 4-fluorophenyl, $R_3$ is $C_1$–$C_6$ alkyl or $C_1$–$C_3$ cycloalkyl, $R_4$ is hydrogen and $R_5$ is phenyl substituted with two or more methoxy groups.

48. A pharmaceutical composition comprising one or more compounds of claim 1.

49. A pharmaceutical composition, useful as hypocholesteromic agent, comprising a hypocholesteromic effective amount of the one or more of the compounds claim 48.

50. A pharmaceutical composition, useful as hypocholesteromic agent, comprising a hypocholesteromic effective amount of 7-[3-(2,4-dimethoxyphenylcarbamoyl)-5-(4-fluorophenyl)-2-(1-methylethyl)-4-phenyl-pyrrol-1-yl]-3R,5R-dihydroxy-heptanoic acid calcium salt with a pharmaceutically acceptable carrier.

51. A pharmaceutical composition, useful as hypocholesteromic agent, comprising a hypocholesteromic effective amount of 7-[3-(2-methoxy-4-hydroxyphenylcarbamoyl)-5-(4-fluorophenyl)-2-(1-methylethyl)-4-phenyl-pyrrol-1-yl]-3R,5R-dihydroxy-heptanoic acid calcium salt with a pharmaceutically acceptable carrier.

52. A pharmaceutical composition, useful as hypocholesteromic agent, comprising a hypocholesteromic effective amount of 7-[3-(2,4-dihydroxyphenylcarbamoyl)-5-(4-fluorophenyl)-2-(1-methylethyl)-4-phenyl-pyrrol-1-yl]-3R,5R-dihydroxy-heptanoic acid calcium salt with a pharmaceutically acceptable carrier.

53. A pharmaceutical composition, useful as hypocholesteromic agent, comprising a hypocholesteromic effective amount of 7-[2-cyclopropyl-3-(2,4-dimethoxyphenylcarbamoyl)-5-(4-fluorophenyl)-4-phenyl-pyrrol-1-yl]-3R,5R-dihydroxy-heptanoic acid calcium salt with a pharmaceutically acceptable carrier.

54. A pharmaceutical composition, useful as hypocholesteromic agent, comprising a hypocholesteromic effective amount of 7-[3-(2,4-dimethoxyphenylcarbamoyl)-4,5-diphenyl5-(4-fluorophenyl)-2-(1-methylethyl)-pyrrol-1-yl]-3R,5R-dihydroxy-heptanoic acid calcium salt with a pharmaceutically acceptable carrier.

55. A pharmaceutical composition, useful as hypocholesteromic agent, comprising a hypocholesteromic effective amount of 7-[4,5-bis(4-fluorophenyl)-3-(2,4-dimethoxyphenylcarbamoyl)-2-(1-methylethyl)-pyrrol-1-yl]-3R,5R-dihydroxy-heptanoic acid calcium salt with a pharmaceutically acceptable carrier.

56. A pharmaceutical composition, useful as hypocholesteromic agent, comprising a hypocholesteromic effective amount of 7-[3-(3,5-dimethoxyphenylcarbamoyl)-5-(4-fluorophenyl)-2-(1-methylethyl)-4-phenyl-pyrrol-1-yl]-3R,5R-dihydroxy-heptanoic acid calcium salt with a pharmaceutically acceptable carrier.

57. A pharmaceutical composition, useful as hypocholesteromic agent, comprising a hypocholesteromic effective amount of 7-[3-(3,4-dimethoxyphenylcarbamoyl)-5-(4-fluorophenyl)-2-(1-methylethyl)-4-phenyl-pyrrol-1-yl]-3R,5R-dihydroxy-heptanoic acid calcium salt with a pharmaceutically acceptable carrier.

58. A pharmaceutical composition, useful as hypocholesteromic agent, comprising a hypocholesteromic effective amount of 7-[4,5-bis(4-fluorophenyl)-2-cyclopropyl-3-(2,4-dimethoxyphenylcarbamoyl)-pyrrol-1-yl]-3R,5R-dihydroxy-heptanoic acid calcium salt with a pharmaceutically acceptable carrier.

59. A pharmaceutical composition, useful as hypocholesteromic agent, comprising a hypocholesteromic effective amount of 7-[5-(3,4-difluorophenyl)-3-(2,4-dihydroxyphenylcarbamoyl)-2-(1-methylethyl)-4-(4-fluorophenyl)-pyrrol-1-yl]-3R,5R-dihydroxy-heptanoic acid calcium salt with a pharmaceutically acceptable carrier.

60. A pharmaceutical composition, useful as hypocholesteromic agent, comprising a hypocholesteromic effective amount of 7-[2-cyclopropyl-5-(3,4-difluorophenyl)-3-(2,4-dihydroxyphenylcarbamoyl)-4-(4-fluorophenyl)-pyrrol-1-yl]-3R,5R-dihydroxy-heptanoic acid calcium salt with a pharmaceutically acceptable carrier.

61. A pharmaceutical composition, useful as hypocholesteromic agent, comprising a hypocholesteromic effective amount of 7-[5-(3,4-difluorophenyl)-3-(2,4-dihydroxyphenylcarbamoyl)-2-(1-methylethyl)-4-phenyl-pyrrol-1-yl]-3R,5R-dihydroxy-heptanoic acid calcium salt with a pharmaceutically acceptable carrier.

62. A pharmaceutical composition, useful as hypocholesteromic agent, comprising a hypocholesteromic effective amount of 7-[5-(3,4-difluorophenyl)-3-(2,4-dimethoxycarbamoyl)-4-(4-fluorophenyl)-2-(1-methylethyl)-pyrrol-1-yl]-3R,5R-dihydroxy-heptanoic acid calcium salt with a pharmaceutically acceptable carrier.

63. A pharmaceutical composition, useful as hypocholesteromic agent, comprising a hypocholesteromic effective amount of 7-[2-cyclopropyl-5-(3,4-difluorophenyl)-3-(2,4-dimethoxycarbamoyl)-4-(4-fluorophenyl)-pyrrol-1-yl]-3R,5R-dihydroxy-heptanoic acid calcium salt with a pharmaceutically acceptable carrier.

64. A pharmaceutical composition, useful as hypocholesteromic agent, comprising a hypocholesteromic effective amount of 7-[5-(3,4-difluorophenyl)-3-(2,4-dimethoxycarbamoyl)-2-(1-methylethyl)-4-phenyl-pyrrol-1-yl]-3R,5R-dihydroxy-heptanoic acid calcium salt with a pharmaceutically acceptable carrier.

65. A method of inhibiting cholesterol biosynthesis in a patient in need of such treatment by administering a pharmaceutical composition as defined by claim 58.

66. A method of inhibiting cholesterol biosynthesis in a patient in need of such treatment by administering a pharmaceutical composition as defined by claim 59.

* * * * *